US011439819B2

(12) United States Patent
Imran (10) Patent No.: US 11,439,819 B2
(45) Date of Patent: Sep. 13, 2022

(54) URETHRAL CATHETERS AND METHODS FOR FACILITATED INTRODUCTION INTO THE URINARY TRACT

(71) Applicant: InCube Labs, LLC, San Jose, CA (US)

(72) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 319 days.

(21) Appl. No.: 16/743,361

(22) Filed: Jan. 15, 2020

(65) Prior Publication Data

US 2020/0188662 A1 Jun. 18, 2020

Related U.S. Application Data

(62) Division of application No. 15/448,501, filed on Mar. 2, 2017, now Pat. No. 10,589,093.

(Continued)

(51) Int. Cl.
*A61M 25/01* (2006.01)
*A61N 1/36* (2006.01)
(Continued)

(52) U.S. Cl.
CPC ..... *A61N 1/36007* (2013.01); *A61M 25/0108* (2013.01); *A61M 25/04* (2013.01);
(Continued)

(58) Field of Classification Search
CPC ...... A61M 2210/1096; A61M 25/0017; A61M 25/0108; A61M 25/04; A61M 25/10;
(Continued)

(56) References Cited

U.S. PATENT DOCUMENTS 5,529,574 A 6/1996 Frackelton
6,338,726 B1 1/2002 Edwards et al.
(Continued)

FOREIGN PATENT DOCUMENTS

CN 203264007 U 11/2013
CN 104162228 A 11/2014
(Continued)

OTHER PUBLICATIONS

European search report and opinion dated Oct. 9, 2019 for EP Application No. 17760859.3.
(Continued)

*Primary Examiner* — Kai H Weng
(74) *Attorney, Agent, or Firm* — Brooks Kushman P.C.

(57) ABSTRACT

Embodiments of the invention provide apparatus, systems and methods for facilitating introduction of a urinary drainage catheter (UDC) into the urinary tract (UT). One embodiment provides a UDC including electrodes for delivering high frequency current to a patient's pudendal nerves to relax the urinary sphincter (US) before passing the UDC therethrough so as reduce the resistance force on the UDC and discomfort to the patient. The electrodes can comprise at least one pair of bipolar electrodes and may be flexible so as to bend and flex within the urethra. The UDC includes one or more lumens including a drainage lumen and an inflation lumen for inflating an anchoring device on the UDC. The UDC can include a pressure sensor to assess relaxation of the US. The UDC may include a second set of electrodes and irrigation lumen for relaxing the US and flushing the urethra with the UDC in place.

26 Claims, 9 Drawing Sheets

Related U.S. Application Data (60) Provisional application No. 62/302,668, filed on Mar. 2, 2016.

(51) Int. Cl.
*A61N 1/05* (2006.01)
*A61M 25/04* (2006.01)
*A61M 25/10* (2013.01)
*A61M 3/02* (2006.01)
*A61M 25/00* (2006.01)

(52) U.S. Cl.
CPC ............ *A61M 25/10* (2013.01); *A61N 1/0514* (2013.01); *A61M 3/0279* (2013.01); *A61M 25/0017* (2013.01); *A61M 2210/1096* (2013.01); *A61N 1/36139* (2013.01)

(58) Field of Classification Search
CPC ... A61M 3/0279; A61M 25/00; A61N 1/0514; A61N 1/36007; A61N 1/36139; A61N 1/36; A61N 1/05
See application file for complete search history.

(56) References Cited

U.S. PATENT DOCUMENTS

| | | |
|---|---|---|
| 8,109,982 B2 | 2/2012 | Naghavi |
| 10,471,255 B2 | 11/2019 | Imran |
| 10,589,093 B2 | 3/2020 | Imran |
| 2008/0065167 A1 | 3/2008 | Boggs et al. |
| 2008/0319504 A1 | 12/2008 | Loushin et al. |
| 2009/0054950 A1 | 2/2009 | Stephens |
| 2010/0262067 A1 | 10/2010 | Chornenky et al. |
| 2012/0226098 A1 | 9/2012 | Bar-Yoseph et al. |
| 2013/0261692 A1 | 10/2013 | Cardinal et al. |
| 2014/0058284 A1 | 2/2014 | Bartol et al. |
| 2014/0058588 A1 | 2/2014 | Vitet et al. |
| 2014/0128766 A1 | 5/2014 | Beran |
| 2014/0249595 A1 | 9/2014 | Chancellor et al. |
| 2014/0309550 A1 | 10/2014 | Iglesias |
| 2015/0126839 A1 | 5/2015 | Li et al. |
| 2015/0328454 A1 | 11/2015 | Lambert |
| 2017/0231547 A1 | 8/2017 | Imran |

FOREIGN PATENT DOCUMENTS

| | | |
|---|---|---|
| DE | 3534124 A1 | 4/1987 |
| JP | 2002301087 A | 10/2002 |
| JP | 2002301087 A | 10/2002 |
| JP | 2008018235 A | 1/2008 |
| KR | 100983879 B1 | 9/2010 |
| WO | WO-2015066617 A1 | 5/2015 |
| WO | WO-2017151986 A1 | 9/2017 |

OTHER PUBLICATIONS

International search report with written opinion dated May 26, 2017 for PCT/US2017/020543.
Notice of Allowance dated Oct. 22, 2019 for U.S. Appl. No. 15/448,501.
Notice of Allowance dated Dec. 30, 2019 for U.S. Appl. No. 15/448,501.
Office action dated Jun. 10, 2019 for U.S. Appl. No. 15/448,501.
Extended European Search Report for EP Application No. 21171353.2 dated Aug. 17, 2021 (7 pages).

URETHRAL CATHETERS AND METHODS FOR FACILITATED INTRODUCTION INTO THE URINARY TRACT

CROSS-REFERENCE TO RELATED APPLICATIONS

This application is a divisional of U.S. patent application Ser. No. 15/448,501, filed on Mar. 2, 2017, now U.S. Pat. No. 10,589,093 issued Mar. 17, 2020, which claims the benefit of priority to Provisional Application No. 62/302,668, filed Mar. 2, 2016, the entire content of which is incorporated herein by reference.

This application is also related to the following U.S. Patent Applications, U.S. patent application Ser. No. 15/410,692, filed Jan. 19, 2017, entitled Systems And Methods For Patient-Enabled Bladder Control, now U.S. Pat. No. 10,471,255 issued Nov. 12, 2019; and U.S. patent application Ser. No. 15/431,621, filed Feb. 13, 2017, entitled Apparatus And Methods For Screening Patients For Bladder Control Via Pudendal Nerve Stimulation, published as U.S. Patent Publication No. 2017/0231547A1 on Aug. 17, 2017; both of which are incorporated by reference herein for all purposes.

BACKGROUND OF THE APPLICATION

1. Field of the Invention

The present invention relates to medical apparatus and methods. More particularly, the present invent relates to urethral catheters and methods for introducing such catheters past the urinary sphincter.

Urethral drainage catheters, better known as Foley catheters, comprise a flexible tube that is passed through the urethra and into the bladder. The tube has two or more separated channels, or lumens, running down its length. One lumen is open at both ends, and allows urine to drain out into a collection bag. Another lumen, or side lumen, typically has a valve on the outside end and connects to a balloon at the tip. The balloon is inflated with sterile water or saline within the bladder just above the bladder neck to anchor the catheter in place.

While generally effective, long term placement of urethral drainage catheters is associated with a number of problems. In particular, urethral drainage catheters tend to become coated over time with a biofilm that obstructs the drainage path, requiring that the catheter be flushed or replaced. Replacement of the catheter requires that the catheter be advanced past the urinary sphincter, and repeated replacements can damage the sphincter and in some cases cause infection. The urinary sphincter is normally closed so that the catheter must physically open the sphincter each time it is replaced in order to reach the bladder.

For these reasons, it would be desirable to provide improved urethral drainage catheters and methods for their introduction past the urinary sphincter as they are advanced to the bladder. Any changes to conventional urethral drainage catheters and their introduction protocols should be minimal, and any cost differential should be more than offset by a reduction in trauma to the patients. At least some of these objectives will be met by the inventions described below.

2. Description of the Background Art

US 2014/0128766 describes a Foley catheter that has been modified to measure temperature in the bladder. US 2014/0249595; US 2014/0058284; US 2014/0058588; and US 2014/0309550 describe catheters and systems for assessing and controlling the urinary sphincter.

SUMMARY OF THE INVENTION

Various embodiments of the present invention provide apparatus and methods for advancing a catheter such as urethral drainage catheter, past a patient's urinary sphincter as the catheter is being placed into the patient's bladder. The urethral drainage catheter is typically referred to as a Foley catheter. To facilitate passage of the drainage catheter past the urinary sphincter, energy is delivered to tissue to stimulate the patient's pudendal nerve to cause the urinary sphincter to relax so that the drainage catheter can be advanced through the urinary sphincter and into the bladder with reduced or minimal resistance force on the catheter from the urinary sphincter. This in turn, allows the draining catheter to be so advanced with reduce pain and/or trauma to the patient's urethra caused by passage of the catheter. The energy delivered is typically high frequency electrical current energy source, and the current is typically delivered by electrodes present on the drainage catheter itself. However, other energy sources are also considered such as microwaves, optical (e.g. from a laser or LED) and acoustical energy (e.g., an acoustical transducer such as piezoelectric transducer). Also, the electrodes may present on another device and or may be delivered by an energy source external to the body. Once the urinary sphincter has been relaxed, the drainage catheter may be advanced to the patient's bladder, a balloon or other anchor on the catheter is deployed, and the catheter left in place to function as an ordinary drainage catheter. Optionally, the energy can be applied when the catheter is withdrawn, and the procedure may be repeated whenever it is necessary to exchange drainage catheters in an individual patient.

In a first aspect, the present invention provides a urinary drainage catheter with a catheter body having a distal end and a proximal end. The catheter body typically comprise a flexible elongated tubing or other flexible member configured for advancement into a patient's bladder through the patient's urethra. In various embodiments, the catheter body can be configured as an ordinary urinary drainage catheter, or Foley catheter, which can be modified as described hereinafter to deliver electrical energy to the patient's pudendal nerve for relaxing the urinary sphincter.

The catheter body will include a drainage lumen extending from the distal end to the proximal end of the catheter body, where the drainage lumen is configured to provide a drainage path for urine when the distal end of the catheter is present in the patient's bladder. The urinary drainage catheter will further include at least one deployable anchor at the distal end of the catheter body, where the anchor is configured to hold the catheter in place when the anchor is deployed in the bladder. As with conventional Foley catheters, the deployable anchor will usually correspond to an inflatable balloon which can be inflated through an inflation lumen within the catheter body. In other embodiments, though, the deployable anchor could be a malecot type (such as malecot wings), an expandable cage, or the like. With particular regard to the present invention, the urinary drainage catheter will have an energy delivery element, such as an electrode(s) at or near its distal end, where the element is configured to deliver energy to induce relaxation of the urinary sphincter. Usually, the energy will be high frequency electrical current which will be delivered to the patient's pudenal nerve(s) to cause relaxation of the urinary sphincter to facilitate passage of the urinary drainage catheter therethrough.

In particular embodiments, the urinary drainage catheter will include at least one nerve stimulation electrode configured to deliver the current to the pudendal nerves, often including at least two nerve stimulation electrodes connected to deliver bipolar high frequency current to the pudendal nerve. For example, a first nerve stimulation electrode may be disposed on one side of the catheter body and a second nerve stimulation electrode may be disposed on the opposite side of the catheter body. The electrodes will typically be located at or near the distal tip of the catheter. They may also correspond to patch, ring or other electrodes known in the medical device arts that are configured for placement on or in the surface of a catheter. In other embodiments, the first nerve stimulation electrode may be located at a first axial location on the catheter body and the second nerve stimulation electrode may be located at a second axial location on the catheter body. Usually, such axially spaced-apart electrodes will comprise ring electrodes or other electrodes which at least partially circumscribe the catheter body. The axially spaced-apart electrodes will also usually be located at or near distal end of the catheter though other positions on the catheter are also contemplated. The spacing between the axially spaced apart electrodes can be selected to achieve optimal stimulation of the pudendal nerve for relaxing the urinary sphincter while minimizing thermal, neurological and other physiologic effects on surrounding nerves and tissue. According to various embodiments the spacing between the ring electrodes can be in a range from about 1 to 25 mm, with particular embodiments of 2, 5, 10, 15 and 20 mm. In additional embodiments the catheter tip area may also include a pressure, force or other sensor for sensing the mechanical resistance or force from the urinary sphincter on the catheter so as to determine when the urinary sphincter is relaxed.

In other embodiments, the electrodes can comprise a semicircular ring or patch. Further, in particular embodiments the semicircular patch or ring may comprise a conformable material (such as a thin metal or polymer strip) to allow the catheter including the electrodes to be advanced into the area of the urethra containing the urinary sphincter without exerting significant mechanical force on the urethra causing pain or discomfort to the patient. In other embodiments of a conformable electrode, the electrodes may comprise an area of the catheter body that has a conductive material adhered or otherwise coated to the catheter surface by a process such as electro-deposition or coating. In such embodiments, the electrode has essentially the same flexibility as the catheter body itself, greatly diminishing any force exerted on the urethra by the electrode during catheter advancement due to increased stiffness of the electrode relative to the catheter body. They also allow the electrode to conform to an inner contour of the urethra In particular designs, the catheter will have a proximal hub or adapter positioned at or near the proximal end of the catheter body. The proximal hub will have at least a first port connected to the drainage lumen, a second port connected to the inflation lumen, and a third port for connecting a cable, wire or other elongated electrical conductors to the at least one nerve stimulation electrode. A cable will typically have a plug or other interface that will be suitable for plugging into a controller, as described hereinafter.

In a second aspect, the invention provides systems for facilitating introduction of a urinary drainage catheter into the urinary tract of a patient comprising a urinary drainage catheter having any or all of the characteristics described above in combination with a controller configured to deliver high frequency current to the nerve stimulation electrode(s) on the urinary drainage catheter. The controller may include its own electrical power source or can be configured to be coupled to an electrical power source such as various AC power supplies. The controller will typically be configured to deliver stimulation current at a frequency above 4 kHz, an amperage below 15 mA, and a voltage in the range from 40V to 60V. The controller will typically be configured to deliver bipolar current to one or more electrode pairs on the catheter, but in other instances could be configured to deliver monopolar current to a single electrode on the drainage catheter and to also connect to a dispersive patch/return electrode on the patient of the type known for use with monopolar high frequency current delivery. The controller can also be configured to limit the total amount of delivered electrical energy/power to stay below that which would injure, burn or damage tissue near the catheter tip including the pudendal nerve. To that end, in particular embodiments, the controller may be configured to receive an input from a temperature or other sensor positioned on the catheter tip (or other location) and utilize that input to control or otherwise regulate the delivery of electrical energy to the electrodes so as to stay below a selected temperature threshold which would injure or otherwise damage tissue near the catheter tip. In these and related embodiments, the controller may include a temperature control algorithm known in the art such as P, PI or PID or other like control algorithm. Such an algorithm can be implemented via an electronic instructions set embedded in a processor or other logic resources incorporated into or operably coupled to the controller.

In a third aspect of the present invention, a method for introducing a urinary drainage catheter through a patient's urethra into the patient's bladder wherein the patient's urinary sphincter is relaxed to reduce the pain, discomfort from advancement of the catheter to the patient from advancement. The method comprises advancing a distal end of the drainage catheter through the urethra until the catheter tip reaches the patient's urinary sphincter. In specific embodiments, end or tip location can be determined by a pressure or other sensor on the tip of the catheter, or through the use of radio-opaque, echogenic or other markers placed on the catheter tip area for imaging purposes. High frequency current is then delivered to the patient's pudendal nerve to relax the urinary sphincter, and the distal tip of the drainage catheter may then be advanced through the urinary sphincter while the sphincter remains relaxed. Relaxation of the sphincter can be determined by imaging or through the use of a pressure/force or other sensor placed on the catheter tip. Once the catheter has successfully passed the urinary sphincter, the distal tip of the drainage catheter can be properly positioned in the patient's bladder in a manner similar to that for positioning ordinary urinary drainage catheters.

In use, embodiments of the invention which provide for relaxation of the urinary sphincter allow a urinary drainage catheter to be placed in the patient's bladder faster and with far less pain and discomfort to the patient as well as reduced incidence of trauma and other injury to the urethra, urinary sphincter and surrounding tissue. In specific embodiments, the urinary sphincter is sufficiently relaxed to keep the force applied to the catheter and/or to the urethra (including the section of urethra in the area of the urinary sphincter) during advancement below a set threshold. For example, the threshold may be below 2 lbs of force, more preferably below 1 lb of force, still more preferably below 0.5 lbs of force and still more preferably below 0.25 lbs of force. Again, the force can be determined by a pressure/force sensor placed on near the drainage catheter tip and/or through other force sensor means. Relaxation of the sphincter can also be assessed in terms of the folds of the urinary sphincter and/or the section on the urethra in the area of the urinary sphincter being substantially effaced. Such effacement can be assessed be via one or more imaging modalities such as video, ultrasound, fluoroscopy and the like as well as pressure measurement. As with the apparatus of the present invention, the methods of the present invention will typically rely on delivering high frequency current through electrodes which are disposed on the drainage catheter itself. Usually, the electrodes will be disposed near the distal tip of the drainage catheter, and the applied current will have the same characteristics as earlier described herein. However, in alternative or additional embodiments, the high frequency current can be delivered by electrodes or other energy delivery device positioned on another catheter, guide wire or similar device positioned within the urethra or via external stimulation. In still other additional or alternative embodiments, the urinary drainage includes another set of electrodes which are positioned proximally to a more distal set so as to stimulate the pudendal nerve to relax the urinary sphincter when the tip of the urinary drainage catheter is positioned in the patient's bladder so as to allow for flushing of the patient urethra from fluid sent through an irrigation lumen in the catheter and existing an aperture positioned on the catheter so as to be positioned proximal to the bladder neck with the drainage catheter is so positioned. In use, such embodiments reduce the risk of urinary tract infection including infection of the urethra and the drainage catheter by allowing the urethra to be flushed of any bacteria or other microorganism present in the urethra or adhered to the drainage catheter.

Also in various embodiments, where high frequency current or other energy is delivered to the pudendal nerve to relax the urinary sphincter, the energy is desirably delivered in a manner which does not cause injury or trauma to the pudendal nerve, urethra or surrounding tissue. In particular embodiments, the characteristics of the delivered current including one or more of frequency, current or voltage can be monitored to be kept below a level which would cause injury to tissue by heating or other phenomena (e.g., electrical toxicity). Also, inputs can be received by one or more thermal sensors positioned on the distal portion of the drainage catheter or other location and used to control one more of the aforementioned characteristics so as to keep the temperature of tissue near the electrodes below a threshold level, for example, 45° C., more preferably below 42.5° C. and still more preferably below 40° C. The inputs can be used in various control algorithms such as PID-based and other like algorithms to maintain the temperature below the threshold point. Such algorithms can be implemented in both hardware or software for example, via electronic instructions embedded in a processor or other logic resource. They can also be used to generate a thermal map of the urethral tissue and other tissue adjacent the electrode so that the physician can have a more comprehensive view of the thermal effect on the tissue during the energy delivery period.

For a fuller understanding of the nature and advantages of the present invention, reference should be made to the ensuing detailed description taken in conjunction with the accompanying drawings. The drawings represent embodiments of the present invention by way of illustration. Accordingly, the drawings and descriptions of these embodiments are illustrative in nature and not restrictive.

BRIEF DESCRIPTION OF THE DRAWINGS

FIGS. 7A-7C illustrate use of an embodiment of the urethral drainage catheter to open the patient's urinary sphincter and deliver irrigation fluid to the patient's urethra with catheter in place in the patients urethra.

DETAILED DESCRIPTION OF THE INVENTION

Embodiments of the invention provide devices, systems and methods for advancing a catheter such as a urethral drainage catheter (typically referred to as a Foley catheter), past a patient's urinary sphincter as the catheter is being placed into the patient's bladder. Many embodiments provide a system, device and method for advancing a catheter, such as a urethral drainage catheter, past the patient's urinary sphincter so as to position the catheter in the patient's bladder wherein energy is delivered by the catheter or other means so as to relax the urinary sphincter during the advancement of the catheter. In use, these and other embodiments reduce the risk of injury, trauma and pain to the patient during the advancement process by reducing the force exerted by the catheter on the urethra, particularly the area adjacent the urinary sphincter. The device will generally comprise an improved or modified urinary drainage catheter having energy-delivery elements or other energy delivery means for delivering energy within the urethra to relax the patient's urinary sphincter in order to facilitate passage of the drainage catheter therethrough. The energy-delivery elements will typically correspond to electrodes, and the electrodes will typically be configured to deliver high frequency current to the patient's pudendal nerve in order to induce relaxation of the urinary sphincter. However, other energy delivery elements capable of delivering other forms of energy are also contemplated including for example, piezo electric elements including elements capable of delivering ultrasonic energy and optical elements such as optical fibers, LEDs, and lasers; and electromagnetic elements such as magnets or electromagnets. The systems of the present invention will typically comprise such modified urinary drainage catheters in combination with a controller having (or operably coupled to) at least a power supply which can deliver the energy which relaxes the urinary sphincter, typically delivering electrical current at a frequency above 4 kHz, at an amperage below 15 mA, and at a voltage from 40V to 60V. However, other frequencies, amperages and voltages are also considered. The methods of the present invention comprise delivering energy to the patient which relaxes the urinary sphincter, and thereafter passing a urinary drainage catheter through the relaxed sphincter in order to reduce the injury or trauma to the urinary sphincter and/or urethra in the area of the urinary sphincter which may occur if the sphincter were not relaxed. Preferably, but not necessarily, the energy will be delivered from electrodes or other energy-delivery elements that are positioned on the catheter itself. In alternative or additional embodiments, the energy may be delivered by another catheter or like device or may be delivered externally by electrodes or other energy delivery elements positioned on an exterior surface of the patient's body in such a manner and location so as to stimulate the patient's pudendal nerve to relax the urinary sphincter.

Figure 1:
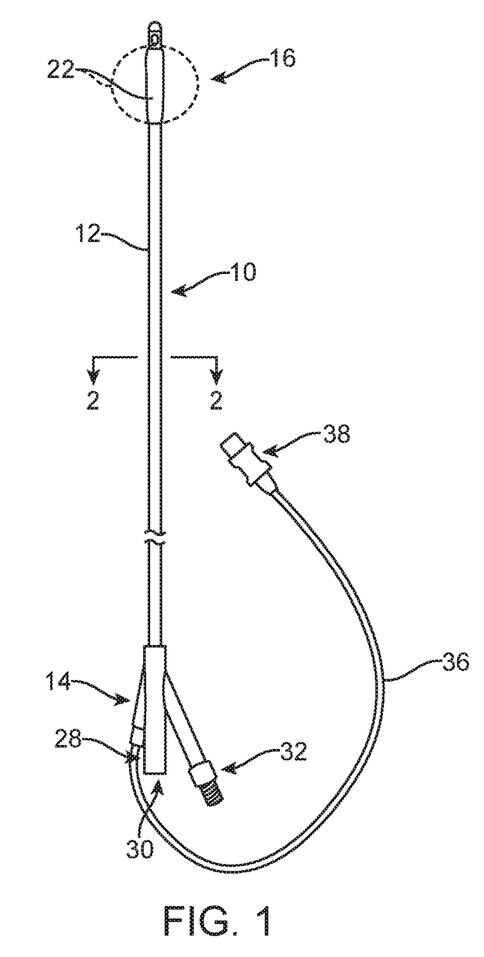
FIG. 1 illustrates an embodiment of a urethral drainage catheter constructed in accordance with the principles of the present invention.
Figure 2:
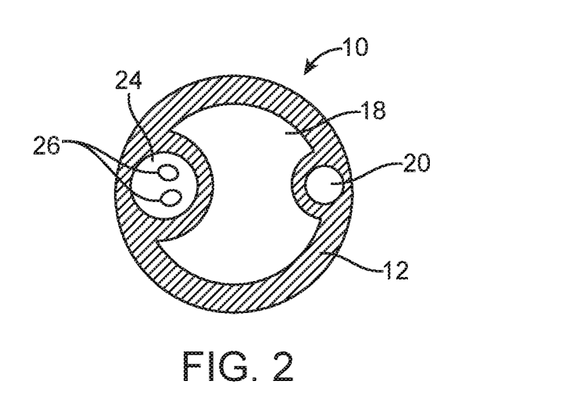
FIG. 2 is a cross-sectional view taken along line 2-2 in FIG. 1.

Referring now to FIGS. 1 and 2, an exemplary embodiment of a urinary drainage catheter 10 constructed in accordance with the principles of the present invention will now be described. Catheter 10 will typically comprise a catheter body 12 having a proximal end 14 and a distal end 16 and one or more lumens including a drainage lumen 18 and inflation lumen 20 for inflating a deployable anchor 22 such as an inflatable balloon. Catheter body 12 will also usually comprise a flexible elongated tube (or other flexible elongated member) having one more lumens. Typically, the drainage lumen 18 will extend from the proximal end 14 to the distal end 16 of the catheter body, but shorter lengths are also contemplated. The catheter body 12 may also include a third lumen 24 which carries cables or wires or other elongated electrical conductor 26 which are used to deliver energy to the distal end of the catheter, as described in more detail below. It may also include an irrigation lumen 25 having a distal aperture 242 for flushing the urethra as is described herein with respect to the embodiments shown in FIGS. 7a-7c. The urinary drainage catheter 10 will usually further include a proximal hub or adapter 28 having a first port 30 which is connected to a proximal end of the inflation lumen 18, a second port 32 connected to the proximal end of the inflation lumen 20, and a third port 34 which passes a cable 36 which carries the conductors 26 to a connector 38. The catheter will also include at least one nerve stimulation electrode 43 for delivering high frequency current to the pudendal nerve to relax the urinary sphincter. In many embodiments the at least one electrode 43 will comprise at least two electrodes as is described in more detail below.

Figure 3A:
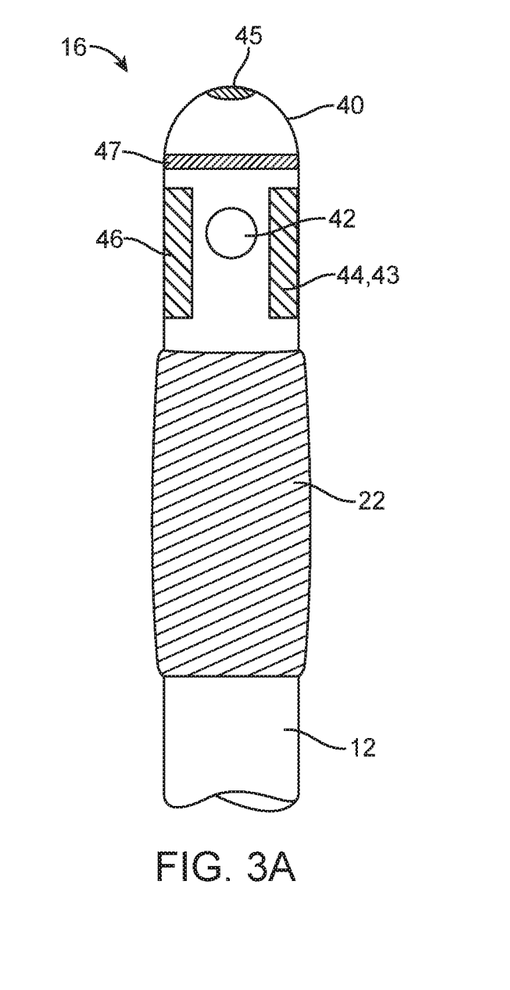
FIGS. 3A and 3B are detailed views of a distal end of the urethral drainage catheter of FIG. 1.
Figure 3B:
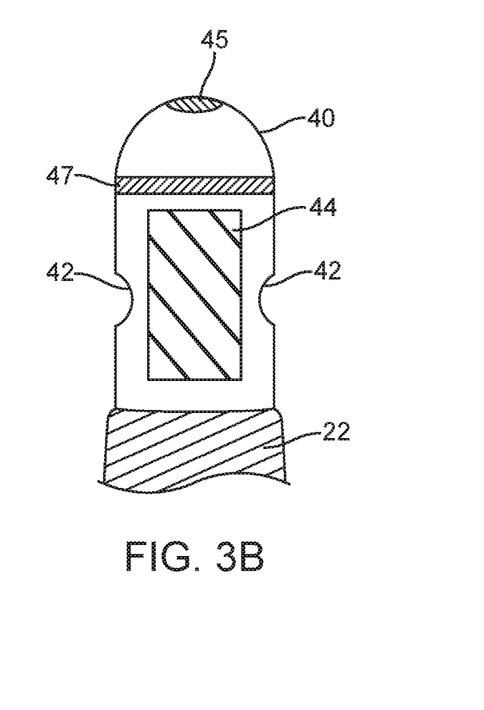

Referring now to FIGS. 3A and 3B, the distal end 16 of the catheter 10 will be described in more detail. The distal end 16 terminates at a distal tip 40 which is typically hemispherical in order to reduce trauma to the urethra and urinary sphincter as the catheter is advanced through the urethra. Other atraumatic tip designs would also be useful. Other atraumatic distal tip 40 shapes are also contemplated. In particular embodiments, the tip may also be tapered (e.g. 05, 45, 60 degrees of taper) to facilitate entry into the area or section of the urethra including the urinary sphincter to minimize the force exerted on the urethral walls and pain and discomfort to the patient. Further, the use of various atraumatic polymers for the tip area are also contemplated, such as silicone, polyurethane, PTFE, etc. The distal end 16 further includes a drain port 42 which opens into the drainage lumen 18 of the catheter body 12. In many embodiments, nerve stimulation electrode 43 comprises at least a first and second nerve stimulation electrode 44 and 46 for delivering high frequency energy to the pudendal nerve so as to stimulate the pudendal nerve to cause relaxation of the urinary sphincter. Electrodes 44 and 46 may be positioned on a surface of the catheter body or they may be recessed. In particular embodiments, first electrode 44 can be radially positioned on one side of the distal end of the catheter body 12 and second electrode 46 can be radially positioned on the opposite side of the catheter body 12 (e.g., about 180° apart). The electrodes 44 and 46 are connected to the connecting wires, cable or other elongated conductor 26 so that they may, in turn, be connected to a controller 50 having an internal or external power supply as is described in more detail below. Electrodes 44 and 46 may correspond to various biocompatible conductive metals known in the art including, for example, gold, platinum, silver and iron based electrodes and alloys thereof. The electrodes may also be configured to be flexible so as bend, flex and otherwise conform to the inner contour of the urethra. In particular embodiments, a flexible nerve stimulation electrode 43 may in the form of a flexible conductive patch configure to bend and flex as so described. Accordingly, in these and related embodiments the electrode materials may correspond to super-elastic materials such as NITINOL or other nickel-titanium alloys as well as various flexible conductive polymers known in the art. In other embodiments of a flexible and/or conformable electrode, electrodes 43 may comprise an area of the catheter body that has a conductive material adhered or otherwise coated to the catheter surface by a process such as electro-deposition or coating. In such embodiments, the electrode has essentially the same flexibility as the catheter body itself, greatly diminishing any force exerted on the urethra by the electrode during catheter advancement due to increased stiffness of the electrode relative to the catheter body.

In various embodiments, the stimulation electrodes 44 and 46 or other electrode 43 may be radially spaced apart on the catheter body in various configurations, for example two electrodes spaced 180° apart, three electrodes spaced 60° apart, four electrodes spaced 45° etc. These electrodes may be configured as bipolar or monopolar electrodes. In the latter case, the catheter tip may also include a reference electrode or an external return electrode as described herein. In the former case, the radially spaced apart electrodes may correspond to pairs of bipolar electrodes radially spaced apart, e.g. a first pair on side of the catheter tip and a second pair radially spaced 180° from the first pair. Also, in various embodiments nerve stimulation electrodes 43 may positioned on the surface of catheter tip 40 or they may recessed a selected amount, for example, between about 0.0001 to about 0.01" (with specific embodiments of 0.001. and 0.005") so as to control the depth of penetration of electrical energy into tissue. Greater amounts of recess generally reduce the depth of penetration of current and energy into tissue as well as the heating depth of tissue.

In various embodiments multiple nerve stimulation electrodes 43 including multiple pairs of nerve stimulation electrodes such as electrodes 44 and 46 may be positioned throughout the length of catheter body 12 so that the electrodes can stimulate the pudendal nerve when the catheter is advanced various amounts within the patient's urinary tract. In the embodiment shown in FIGS. 7a-7c a second set of nerve stimulation electrodes 244 and 246 (which may be bipolar electrodes) can be positioned proximally to electrodes 44 and 46 so that the pudenal nerve can be stimulated to relax the urinary sphincter US when the catheter body 12 is fully advanced in the urinary tract such that the catheter distal end 16 is positioned within the patients bladder B.

In various embodiments, the invention also provides systems for facilitating introduction of a urinary drainage catheter into the urinary tract of a patient. One embodiment of such a system 52 comprising a urinary drainage catheter 10 having any or all of the characteristics described above in combination with a controller 50 configured to deliver high frequency current to the nerve stimulation electrode(s) on the urinary drainage catheter. The controller 50 may include its own electrical power source 54 (which may be an AC power supply) or can be configured to be coupled to an external electrical power source (not shown) such as various AC power supplies. The controller 50 will typically be configured to deliver stimulation current at a frequency above 4 kHz, an amperage below 15 mA, and a voltage in the range from 40V to 60V. The controller will typically be configured to deliver bipolar current to one or more electrode pairs on the catheter, but in other instances could be configured to deliver monopolar current to a single electrode on the drainage catheter and to also connect to a dispersive patch/return electrode on the patient of the type known for use with monopolar high frequency current delivery. The controller can also be configured to limit the total amount of delivered electrical energy/power to stay below that which would cause pain to the patient and/or injure, burn or otherwise damage tissue near the catheter tip including the pudendal nerve.

Prevention of thermal or other injury to the urethra and pudendal nerve can be accomplished through a variety of means including control of the characteristics of the electrical energy delivered including current, frequency and voltage. In particular embodiments, such control can be effectuated through the use of one or more thermal sensors 49 positioned in or on catheter body 12 in the area of electrodes 44 and 46 tip or other location on the catheter body to provide temperature information to control one more of the aforementioned characteristics so as to keep the temperature of tissue near the electrodes below a threshold level, for example, 45° C., more preferably below 42.5° C. and still more preferably below 40° C. Sensors 49 may correspond to one or more thermal sensors known in the art including thermistors and thermocouples and they may be operatively coupled (e.g. electronically coupled) to controller 50. Inputs 49i encoding information from such thermal sensors 49 can be used in various control algorithms such as P, PI or PID based and other like algorithms to maintain the tissue temperature below the threshold point. Such algorithms can be implemented in both hardware or software for example, via electronic instructions or module embedded in controller 50 or other logic resources used by catheter 10. Such inputs 49i can also be used to generate a thermal map of the urethral tissue and other tissue adjacent the electrode so that the physician can have a more comprehensive view of the thermal effect on the tissue during a current/energy delivery period.

Prevention of thermal or electrical injury to the urethra and pudendal nerve can in various embodiments, also be achieved by control of the shape and area of the electrode or other energy delivery element. For example in specific embodiments, the area of the electrodes can range from about 0.1 mm to 100 mm², with specific embodiments of 0.5, 1, 2.5, 5, 10, 20, 25, 50, 75 and 80 mm². Larger areas can be used to reduce current density at a given electrode and in turn the degree of ohmic heating of tissue. According to various embodiments, shapes for the electrodes which can be employed to reduce pain or injury from ohmic heating, include those having rounded edges such as circular, oval or rectangular with rounded edges (e.g., due to edge effects from higher current densities). Specific embodiments of the invention provide an inventory of electrodes or other energy delivery elements for the urinary drainage catheters described herein, with various areas and shapes (e.g. circular, oval, etc.) which reduces pain and injury to the urethra and surrounding tissue including the urinary sphincter US and pudendal nerve. According to one or more embodiments, electrodes 44, 46 (or other electrode) having selected sizes and shapes can be configured to be removably fitted (e.g. by a snap or press fit or other means known in the catheter arts) on to the catheter distal end 16. Once fitted, the physician can then advance the catheter into the urethra and do several test deliveries of electrical energy to determine if the electrode causes any pain or discomfort to the patient. Alternatively, the electrode size and shape can be selected based on patient parameters such as size, weight, age, medical condition etc., relative to a population of those patients having those characteristics, in particular relative to the patient population in which the electrode characteristics (e.g., area, shape and material) do not cause pain or injury to the patient from ohmic heating.

Figure 4A:
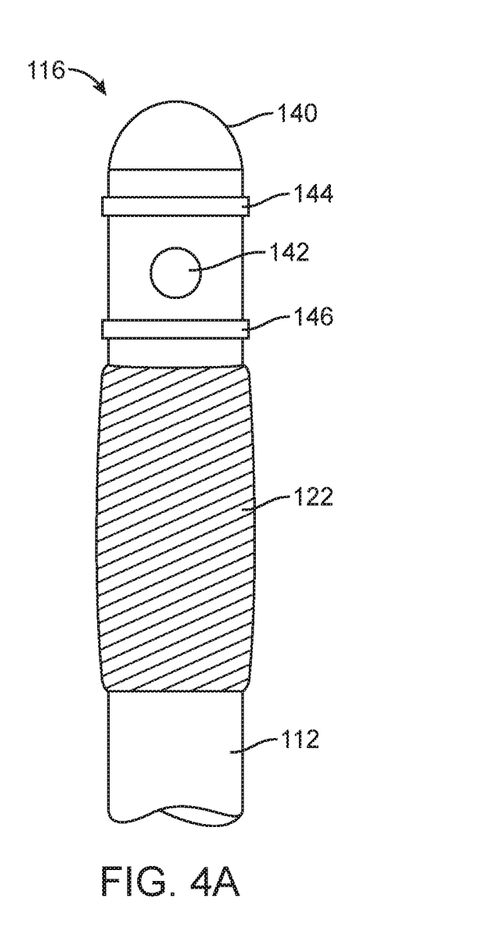
FIGS. 4A and 4B are detailed views of an alternative distal end of the urethral drainage catheter of FIG. 1.
Figure 4B:
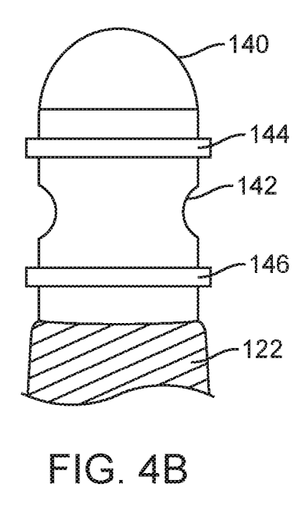

An alternative embodiment of a distal end 116 of the catheter 110 is illustrated in FIGS. 4A and 4B. In this and related embodiments, the distal end 116 includes a distal tip 140, drain port 142, and inflatable balloon 122, all of which are similar or identical to those described in connection with FIGS. 3A and 3B. Instead of patch or surface electrodes 44 and 46, however, the embodiment of FIGS. 4A and 4B includes ring electrodes 144 and 146 which are axially spaced-apart near the distal tip 140, usually being located on either side of the drain port 142. The electrodes 144 and 146 may be connected to the wires or conductors 26 as described previously for electrodes 44 and 46. While both illustrated embodiments include electrode pairs and are intended particularly for use with bipolar power supplies, single patch, surface, ring, or other electrodes could be used with monopolar power supplies which use an external or dispersive electrode placed on the patient's lower back or thigh. In alternative of additional embodiments, the electrodes may comprise tripolar electrode for use with a tripolar power supply.

Figure 5:
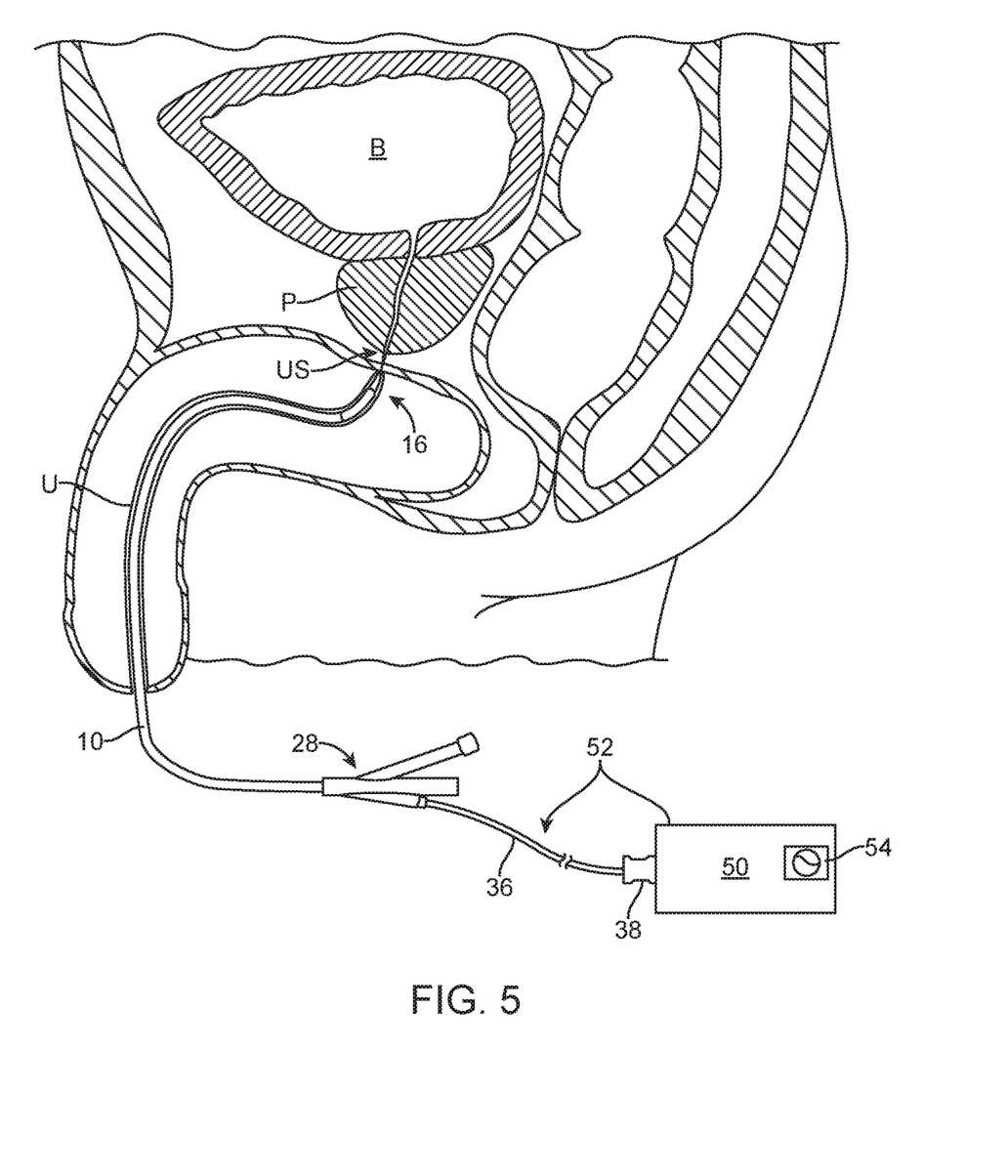
FIG. 5 illustrates the urethral drainage catheter of FIG. 1 advanced into a patient's urethra at a location just before a urinary sphincter.

Referring now to FIG. 5, the urinary drainage catheter 10 may be introduced to a bladder B by first passing the distal end 16 of the catheter upward through the patient's urethra U. Advancement of the catheter 10 will be generally the same as for any Foley or other urinary drainage catheter until the distal end 16 of the catheter reaches the urinary sphincter US. Once the distal end 16 reaches the urinary sphincter, which may be detected by manually detecting an increased resistance to advancement, the user may energize controller 50 to deliver a stimulating current through the catheter electrodes 44 and 46. The urinary sphincter is anatomically close to the patient's pudendal nerves, and delivery of current through the urethral wall will stimulate the pudendal nerves. The particular frequencies, current levels, and voltages described above are known to induce relaxation of the urinary sphincter.

Figure 6A:
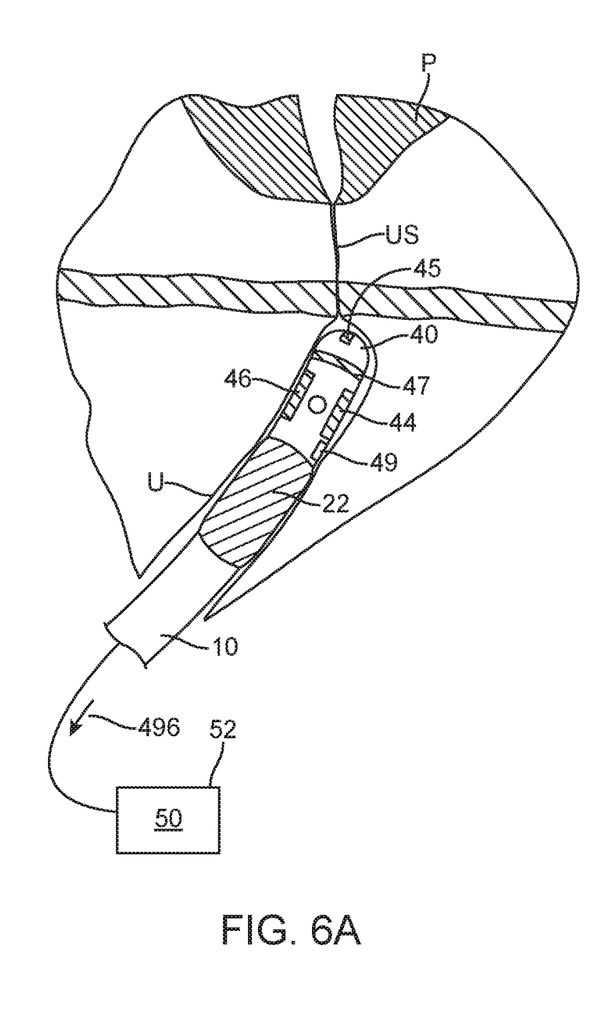
FIGS. 6A-6C illustrate advancement of the urethral drainage catheter of FIG. 1 past the patient's urinary sphincter using the delivery of high frequency current in accordance with the methods of the present invention.
Figure 6B:
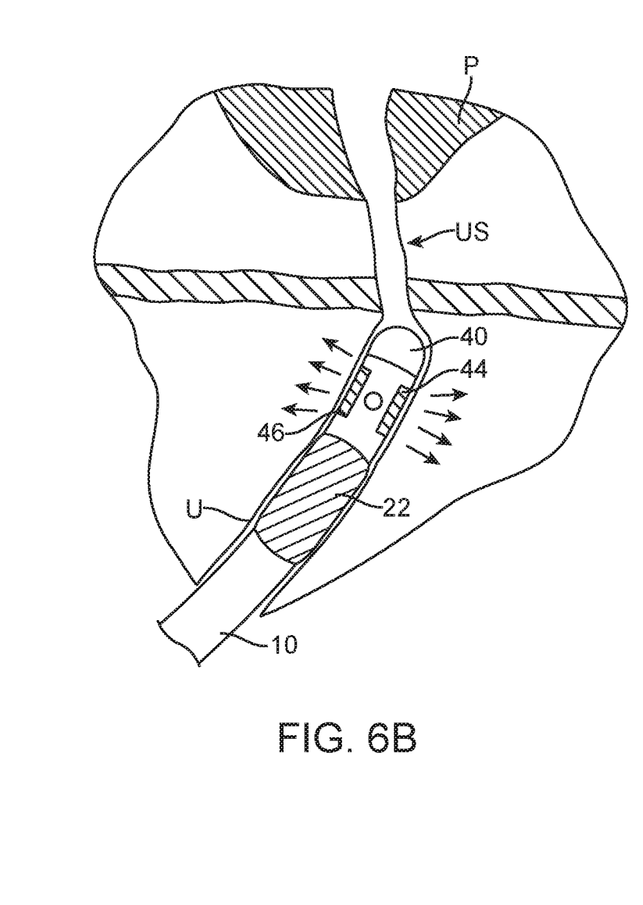
Figure 6C:
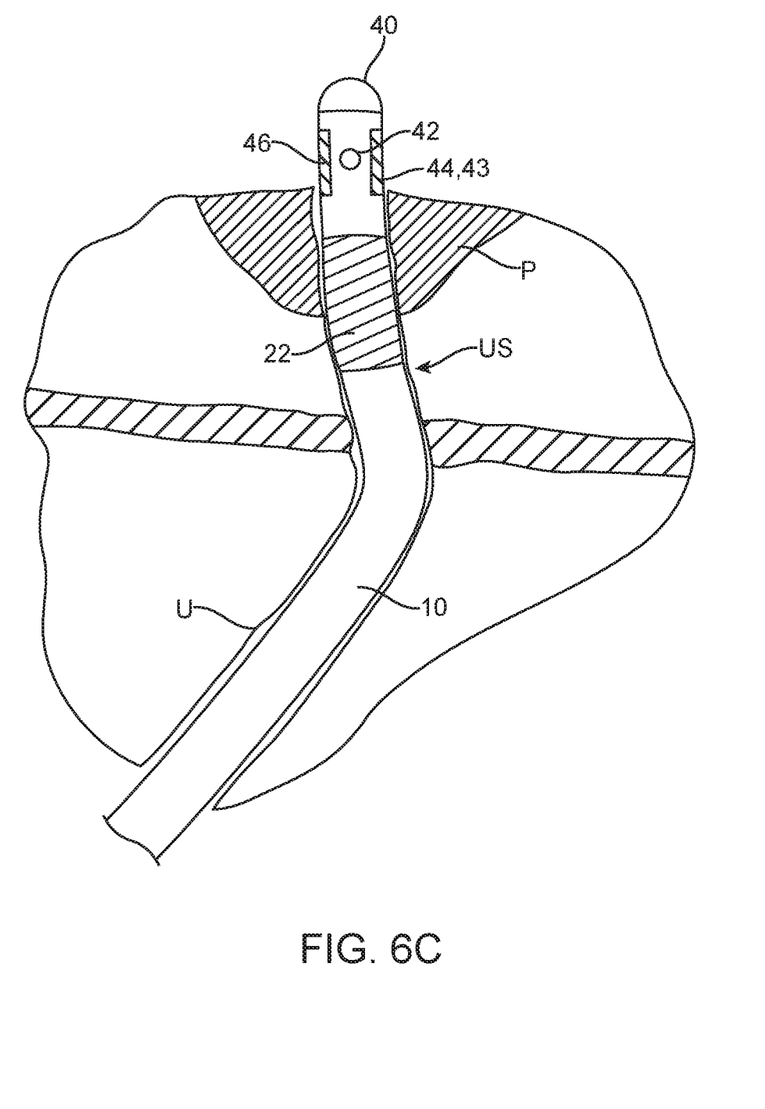

Referring now to FIGS. 6A-6C, during advancement of catheter 10 distal tip 40 of the catheter 10 first reaches the urinary sphincter US with the sphincter generally constricted or closed, as shown in FIG. 6A. The stimulating current may then be delivered through electrodes 44 and 46, as generally shown in FIG. 6B, in order to open or otherwise relax the urinary sphincter US. Once the urinary sphincter is relaxed or open, the distal tip 40 of the catheter 10 may be advanced through the relaxed urinary sphincter so that it easily passes beyond the sphincter into the prostate P (in male patients)

and eventually into the bladder where it functions as a normal urinary drainage catheter, as shown in FIG. 6C. According to one or more embodiments, relaxation or opening of the urinary sphincter US may be sensed by pressure/force sensor or other sensor 45 which may be placed at or near the distal tip 40 of catheter 10 and/or nearby (e.g. within several mm's) of electrodes 44 and 46 Such sensors may correspond to various solid state pressure sensors such as a various solid state strain gauges known in the art including mems-based sensors. According to one or more embodiments sensor 45 is configured to send an input to controller 50 including information on a sensed pressure or force by the sensor. Sensor 45 may also be used to sense when the distal tip of the catheter 40 has been positioned in the patient's bladder B by sensing a decrease or other change in pressure.

According to one or more embodiments controller 50 can also be configured to limit the total amount of delivered electrical energy/power to stay below that which would injure, burn or otherwise damage tissue near the catheter tip including the pudendal nerve. To that end, in particular embodiments, the controller 50 may be configured to receive an input from a temperature or other sensor 49 positioned on or near catheter tip 40 and utilize that input to control or otherwise regulate the delivery of electrical energy to the electrodes so as to stay below a selected temperature threshold which would injure or otherwise damage urethral or other tissue near the catheter tip. In these and related embodiments, the controller may include a temperature control algorithm known in the art such as P, PI or PID or other like control algorithm. Such an algorithm can be implemented via an electronic instructions set embedded in a processor or other logic resources incorporated into or otherwise in communication with controller 50.

In related embodiments, the characteristics of the high frequency current or other energy used to relax the urinary sphincter can be tuned or otherwise adjusted to improve or optimize relaxation of the urinary sphincter. Such tuning or adjusted by measurement of urinary sphincter pressure using a pressure sensor 45 or other sensor coupled to catheter or another device. In particular, the high frequency current may be "tuned" (grossly adjusted) or "finely tuned" (finely adjusted) while observing or tracking changes in urinary sphincter pressures so as to identify those settings which result in a selected and/or maximum decrease in urinary sphincter pressure. Gross adjustments may incorporate changes in the range of about 5 to about 25%, while fine adjustments may those less than about 5%. Specific adjustments may be made in one or more characteristics of the high current including of the frequency, current or voltage of the wave as well as the shape of the wave. In particular, adjustments may be made in in the peak amplitude of the current or voltage as well as the RMS amplitudes. Also different waveforms may employed including for example sine wave, square wave and saw tooth waves. Also, in one or more embodiments, the waveform may in the form of biphasic pulses with a selectable pulse width, for example 1 to 100 ms. Further description of methods and approaches for tuning the characteristic of the high frequency current to relax the urinary sphincter may be found in the U.S. patent application Ser. No. 15/431,621, entitled Apparatus And Methods For Screening Patients For Bladder Control Via Pudendal Nerve Stimulation, filed Feb. 9, 2017, which is fully incorporated herein by reference for all purposes.

Other embodiments of the invention provide methods for introducing a urinary drainage catheter through a patient's urethra into the patient's bladder wherein the patient's urinary sphincter is relaxed prior to or during advancement of the catheter so as to reduce one or more of the pain, discomfort to the patient from advancement of a drainage catheter into the bladder B. In one embodiment, the method comprises advancing the end 16 of the drainage catheter 10 through the urethra until the distal tip 40 reaches the patient's urinary sphincter US. In specific embodiments, tip location within the urethra can be determined by a pressure/force or other sensor 45 positioned on the tip 40 of the catheter 10, or through the use of radio-opaque, echogenic or other marker 47 placed on the distal end 16 or distal end area for imaging purposes or both. High frequency current is then delivered to the patient's pudendal nerve to relax the urinary sphincter, and the distal tip of the drainage catheter may then be advanced through the urinary sphincter US while the sphincter remains relaxed. Relaxation of the sphincter can be determined by imaging or through the use of a sensor 45 placed on the catheter end 16 or tip 40 as described above. Once the catheter has successfully passed the urinary sphincter US, the distal tip 40 of the drainage catheter 10 can be properly positioned in the patient's bladder in a manner similar to that for positioning ordinary urinary drainage catheters. Then the deployable anchor of the catheter typically, an inflatable balloon is inflated to anchor the distal portion of the catheter in place in the bladder. Once so anchored, in a similar function to a Foley catheter, catheter 10 can then drain urine from the bladder through the drainage lumen 18. Optionally, energy can be delivered by the electrodes when the catheter is withdrawn so as to reduce pain and the risk of ureteral trauma or injury to the patient, and the procedure may be repeated whenever it is necessary to exchange drainage catheters in an individual patient.

In specific embodiments, energy is applied to the pudendal nerve such that urinary sphincter is sufficiently relaxed to keep the force applied to the catheter and/or to the urethra (including the section of urethra in the area of the urinary sphincter) during advancement below a set threshold. For example, the threshold may be below 2 lbs of force, more preferably below 1 lb of force, still more preferably below 0.5 lbs of force and still more preferably below 0.25 lbs of force. Again, the force can be determined by a pressure/force sensor placed on near the drainage catheter tip and/or through other force sensor means. Relaxation of the sphincter can also be assessed in terms of the folds of the urinary sphincter and/or the folds in the section on the urethra in the area of the urinary sphincter being effaced. Desirably the folds are substantially effaced (substantially in this case being about 90% in terms of a ridge or valley in the urinary sphincter or urethra), though lesser amounts of effacement are also contemplated. Such effacement can be assessed be via one or more imaging modalities such as video, ultrasound, fluoroscopy and the like as wells as by pressure measurement.

Figure 7A:
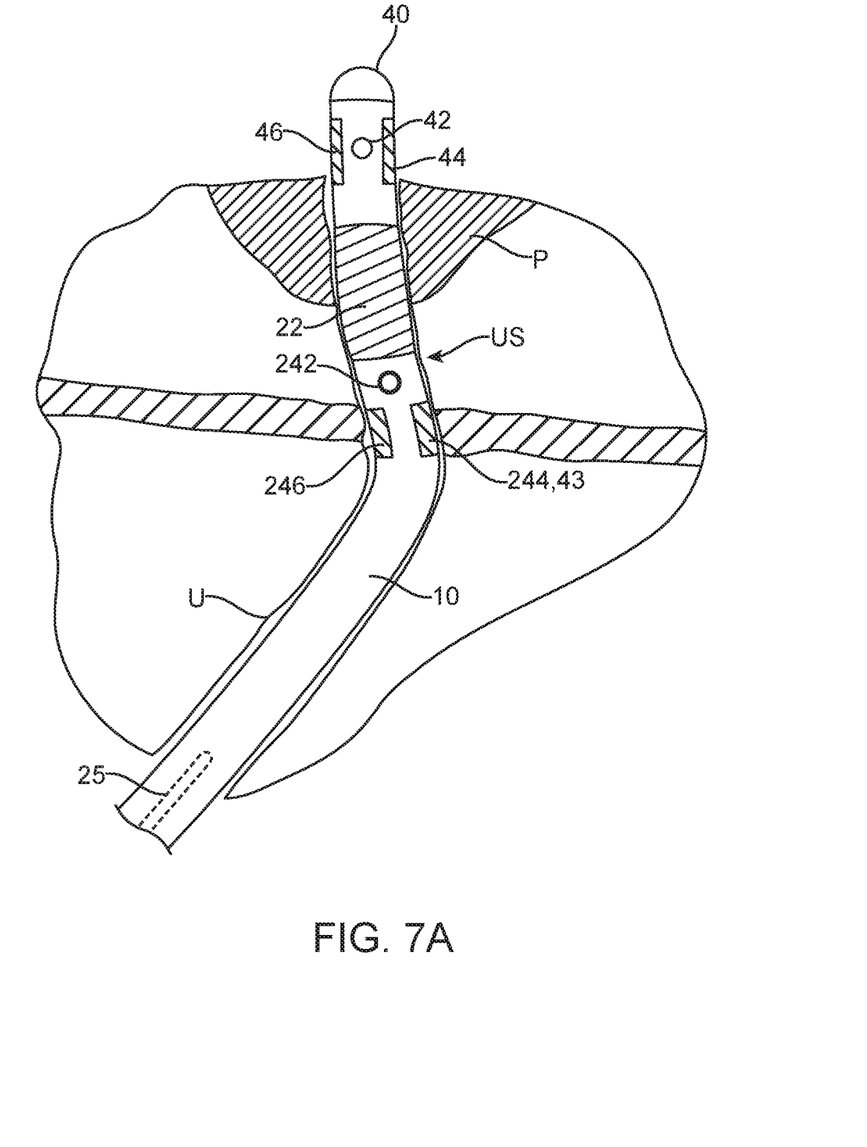
FIG. 7A shows the catheter fully advanced with the urinary sphincter and urethra contracted against the drainage catheter
Figure 7B:
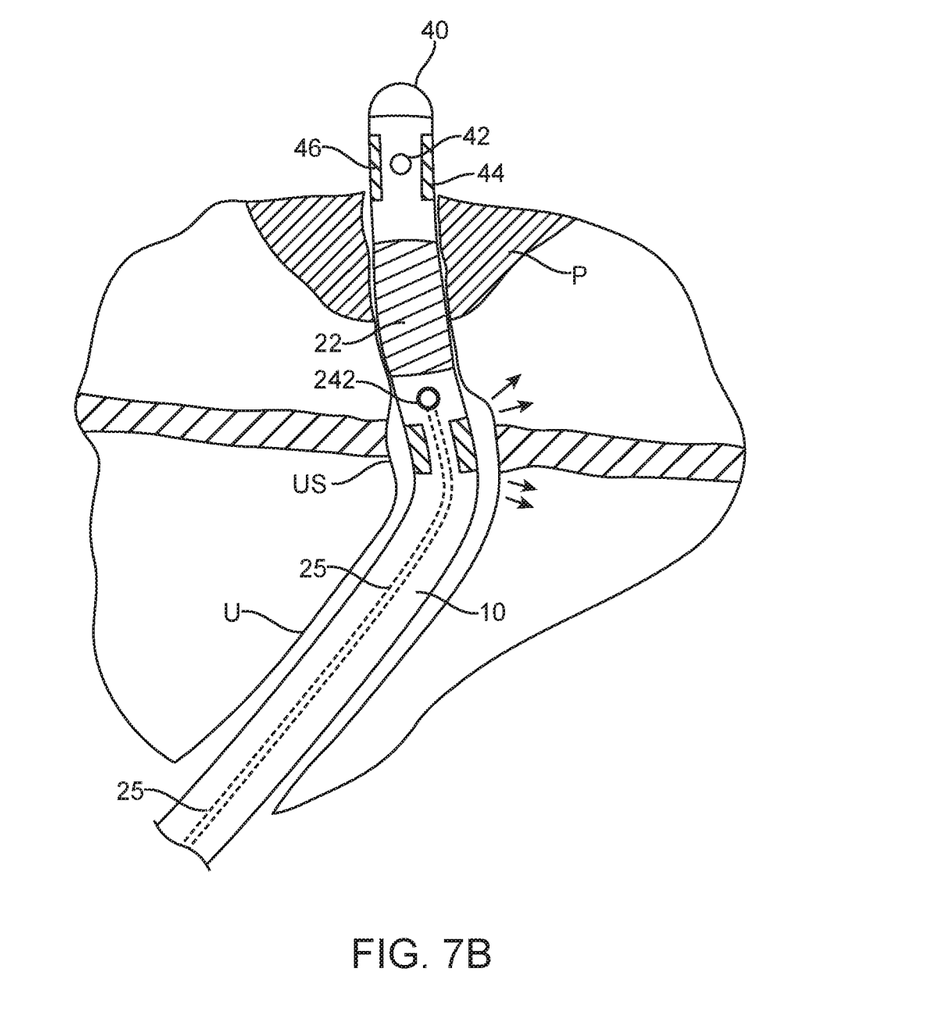
FIG. 7B illustrates delivery of electrical energy to relax and open the urinary sphincter and urethra.
Figure 7C:
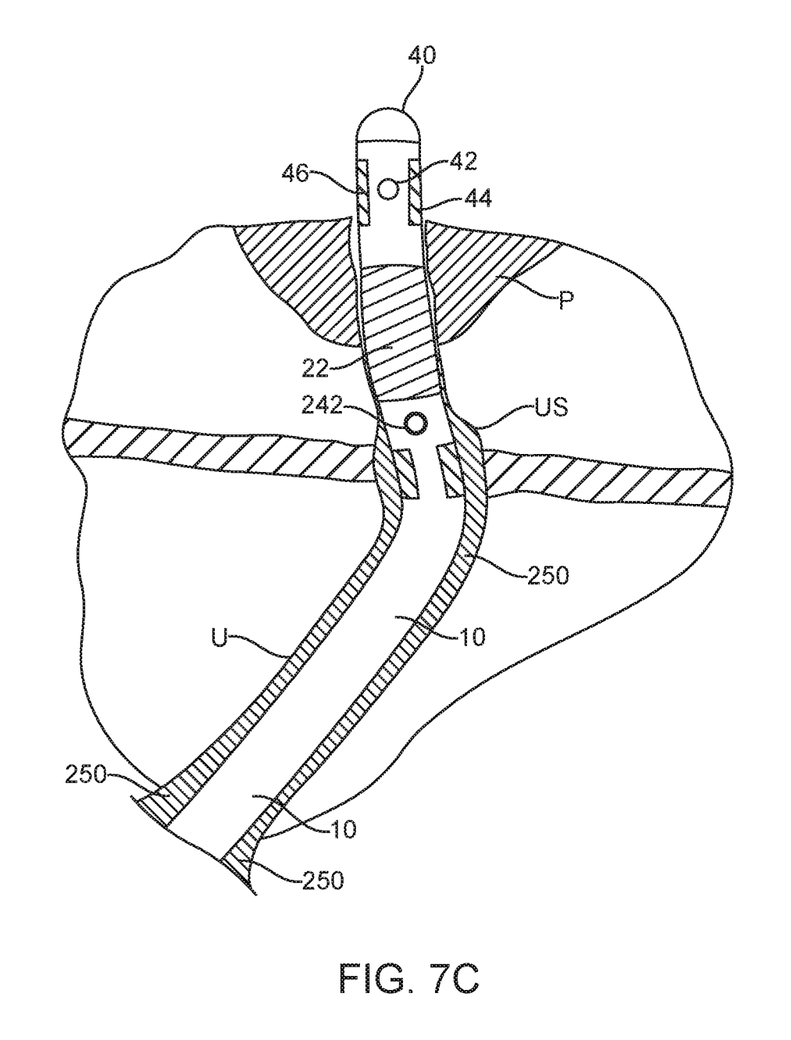
FIG. 7C shows the delivery of an irrigation fluid to flush the urethra with the urinary sphincter opened to allow irrigation fluid to flow completely out of the urethra.

Referring now to FIGS. 7a-7c, in alternative or additional embodiments, high frequency current or other energy can be periodically delivered to the pudendal nerve by catheter 10 so as to flush the patient's urethra. The electrode of the group of electrodes for doing so can be the same or different from the electrode or group of electrodes used stimulate the pudendal nerve when catheter is being advanced near the patient's urinary sphincter. According to one embodiment of a method for doing so using a different group of electrodes, high frequency current can be delivered by an embodiment of the drainage catheter 10 having electrodes 244 and 246 with the distal tip 40 of the catheter positioned in the patient's bladder so as to relax the urinary sphincter US (as described above, electrodes 244 and 246 are positioned proximally on catheter 10 so that are in the areas of the urinary sphincter US when the catheter tip 40 is positioned in the bladder). Then saline or other irrigation fluid 250 can be delivered through an irrigation lumen 25 out of an irrigation port or aperture 242 on catheter 10 so as to flow through and out the urethra to flush the urethra and catheter 10 of any bacteria or other infectious microorganisms (e.g., fungus etc.). In use, such embodiments can significantly reduce the risk of a urinary tract infection, including infection of the urinary drainage catheter that often occurs when a Foley or other urinary drainage catheter is left in place in the patient's urinary tract for an extended period of time. It also allows the same urinary drainage catheter to remain in place for longer time period to time without the need for periodic replacement saving time and expense and reducing patient discomfort from repeated removal and insertion of a new catheter each time.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Further many modifications are contemplated by embodiments of the invention including modifications in size, current characteristics, to accommodate various pediatric and even neonatal applications. Hence, the scope of the present invention is not limited to the specifics of the described embodiments, but is instead limited solely by the appended claims.

What is claimed is:

1. A urinary drainage catheter comprising:
an elongated flexible catheter body shaped and configured for advancement into a patient's bladder through the patient's urethra; the catheter body having a distal end and proximal end, the distal end terminating at a distal tip, and a drainage lumen extending from the distal end to the proximal end of the catheter body to provide a urine drainage path when the distal end of the catheter is positioned in the patient's bladder;
at least one deployable anchor positioned near the distal end of the catheter body, the anchor configured to hold the catheter in place when the anchor is deployed in the bladder; and
at least one nerve stimulation electrode positioned at the distal end of the catheter body, the nerve stimulation electrode configured and positioned on the catheter body so as to be in proximity to a pudendal nerve of the patient to deliver a high frequency current to the patient's pudendal nerve to relax the patient's urinary sphincter as the distal tip of the catheter body is at the urinary sphincter to promote advancement of the catheter body through the urinary sphincter and into the bladder via a reduced resistance force from the urinary sphincter.

2. The urinary drainage catheter of claim 1, further comprising an elongated conductor positioned within the catheter body and having a proximal and distal end, the distal end electrically coupled to the at least one nerve stimulation electrode and the proximal end positioned near the proximal end of the catheter body.

3. The urinary drainage catheter of claim 2, wherein the elongated conductor comprises a wire or a cable.

4. The urinary drainage catheter of claim 1, wherein the at least one nerve stimulation electrode comprises a flexible electrode configured to conform to a contour of the patient's urethra.

5. The urinary drainage catheter of claim 4, wherein the flexible electrode comprises a patch electrode.

6. The urinary drainage catheter of claim 4, wherein the flexible electrode comprises a conductive coating.

7. The urinary drainage catheter of claim 1, the catheter further comprising at least two nerve stimulation electrodes configured to deliver bipolar high frequency current to the patient's pudendal nerve.

8. The urinary drainage catheter of claim 7, wherein a first nerve stimulation electrode is at a first axial location on the catheter body and a second nerve stimulation electrode is at a second axial location on the catheter body.

9. The urinary drainage catheter of claim 8, wherein the first and second electrodes are axially spaced apart by in a range from about 5 to 25 mm.

10. The urinary drainage catheter of claim 8, wherein the first and second electrodes are ring electrodes.

11. The urinary drainage catheter of claim 7, wherein a first nerve stimulation electrode is at a first radial location on the catheter body and a second nerve stimulation electrode is at a second radial location on the catheter body.

12. The urinary drainage catheter of claim 11, wherein the first and second nerve stimulation electrodes are radially spaced apart from another by about 180°.

13. The urinary drainage catheter of claim 1, wherein the deployable anchor comprises an inflatable balloon connected to an inflation lumen in the catheter body.

14. The urinary drainage catheter of claim 13, further comprising a proximal hub positioned at the proximal end of the catheter body, the proximal hub having a first port connected to the drainage lumen, a second port connected to the inflation lumen, and a third port for electrically connecting a cable to the at least one nerve stimulation electrode.

15. The urinary drainage catheter of claim 1, wherein the catheter distal tip comprises an atraumatic tip.

16. The urinary drainage catheter of claim 15, wherein the atraumatic tip comprises a tapered tip or a hemispherical tip.

17. The urinary drainage catheter of claim 1, further comprising an irrigation lumen for irrigating the patient's urethra with the drainage catheter in place, the irrigation lumen extending from the proximal end to a distal portion of the catheter body and having a distal opening for the release of fluid to irrigate or flush the patient's urethra.

18. The urinary drainage catheter of claim 1, further comprising a pressure sensor positioned on the catheter body for measuring a urinary sphincter pressure.

19. The urinary drainage catheter of claim 18, wherein the pressure sensor is positioned on the catheter body near the at least one stimulation electrode or the distal end of the catheter.

20. The urinary drainage catheter of claim 1, further comprising a temperature sensor positioned on the catheter body for measuring tissue temperature near the at least one nerve stimulation electrode.

21. A system comprising:
a urinary drainage catheter as in claim 1; and
a controller configured to deliver a high frequency current to the at least one nerve stimulation electrode to relax the urinary sphincter.

22. The system of claim 21, further comprising an electrical power source for generating the high frequency current, the power source operatively coupled to the controller.

23. The system of claim 22, wherein the power source is internal to the controller.

24. The system of claim 21, wherein the controller is configured to deliver current at a frequency above 4 kHz, an amperage below 15 mA, and a voltage in a range from 40V to 60V.

25. The system of claim 21, wherein the controller is configured to deliver bipolar current to first and second electrodes on the urinary drainage catheter.

26. A system for facilitating urinary drainage of a patient, the system comprising:

- an elongated flexible catheter body shaped and configured for advancement into a patient's bladder through the patient's urethra; the catheter body having a proximal end and a distal end terminating at a distal tip, and a drainage lumen extending from the distal end to the proximal end of the catheter body to provide a urine drainage path when the distal end of the catheter is positioned in the patient's bladder;
- at least one deployable anchor positioned near the distal end of the catheter body, the anchor configured to hold the catheter in place when the anchor is deployed in the bladder;
- at least one nerve stimulation electrode positioned at the distal end of the catheter body, the nerve stimulation electrode configured and positioned on the catheter body so as to be in proximity to a pudendal nerve of the patient when the distal tip of the catheter body is located within the urethra at the urinary sphincter; and
- a controller coupled to the at least one stimulation electrode, the controller comprising a processor and instructions executable on the processor for controlling delivery of a high frequency current from the least one stimulation electrode through the urethral wall and to the patient's pudendal nerve, the high frequency current formulated to relax the patient's urinary sphincter to thus promote advancement of the catheter body through the urinary sphincter and into the bladder via a reduced resistance force from the urinary sphincter.

* * * * *